United States Patent
Majumder et al.

(10) Patent No.: US 6,231,862 B1
(45) Date of Patent: May 15, 2001

(54) PURIFIED NEW EPIDIDYMAL FORWARD MOTILITY PROTEIN AND A PROCESS FOR THE ISOLATION OF THE SAID EPIDIDYMAL FORWARD MOTILITY PROTEIN USEFUL AS A FERTILITY PROMETER/BLOCKER

(75) Inventors: Gopal Chandra Majumder; Bijay Shankar Jaiswal, both of West Bengal (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/203,093

(22) Filed: Dec. 1, 1998

(30) Foreign Application Priority Data

Feb. 26, 1998 (IN) ......................................................... 505/98

(51) Int. Cl.[7] .............................. A61K 39/00; A61K 38/14
(52) U.S. Cl. ...................................... 424/184.1; 424/178.1; 530/350; 530/395; 530/403

(58) Field of Search ...................................... 530/350, 395, 530/403; 424/278.1, 184.1

(56) References Cited

PUBLICATIONS

Mandal et al. Biology of Reproduction, 41 983–989 May 1989.*

Chatterjee et al Biochim. Biophys. Res. Commun., 162, 550–556 Jul. 1989.*

* cited by examiner

Primary Examiner—Michael Borin
(74) Attorney, Agent, or Firm—Ladas & Parry

(57) ABSTRACT

The subject invention relates to a new forward motility protein isolated from goat epididymal plasma and a process for the isolation of the said epididymal forward motility protein useful as a fertility promoter/blocker comprising subjecting goat epididymal plasma to multiple fractionations till purification to obtain purified new epididymal forward motility protein by the chromatographic method.

8 Claims, No Drawings

PURIFIED NEW EPIDIDYMAL FORWARD MOTILITY PROTEIN AND A PROCESS FOR THE ISOLATION OF THE SAID EPIDIDYMAL FORWARD MOTILITY PROTEIN USEFUL AS A FERTILITY PROMETER/BLOCKER

FIELD OF INVENTION

The present invention relates to a purified new epididymal forward motility protein and a process for the isolation of the said epididymal forward motility protein useful as a fertility promoter/blocker. The process of the present invention particularly relates to a process for the isolation of a purified new epididymal forward motility protein from goat, useful as a fertility promoter as well as a fertility blocker.

BACKGROUND OF THE INVENTION

The forward motility protein (FMP) has potential for use as a contraceptive vaccine to control population growth. FMP has also the potential to rectify some of the problems of human infertility(due to low sperm motility): a great social curse in all human races. It has also the potential for solving some of the problems of animal breeding (due to inadequate sperm motility) thereby enhancing milk and meat production.

Population explosion is a major problem in all developing countries including India. Although several contraceptive methods are available, they have undesirable side effects/lower efficacy. In addition some of these methods are rather expensive.

Another global social problem is human infertility. Approx 15% of couples are believed to be infertile. One reason for human infertility is due to low sperm motility. Although several sophisticated Assisted Reproductive Technologies (e.g. IVF: in vitro Fertilization, ICST: Intracytoplasmic Sperm Injection) are available to solve the problems of oligospermic and asthenozoospermic patients (with low sperm motility), these technologies are highly expensive and the success rate is extremely low.

To solve the problem of population explosion and human infertility, it is essential to have an in-depth understanding of the biochemical basis of the reproductive processes. The following section briefly reviews the literature on epididymal sperm maturation: an important event in the male reproductive function.

Mammalian testicular spermatozoa are immotile and infertile. During transit through epididymis these cells acquire forward motility which is essential for their ability to fertilize the female eggs. Biochemical basis of the epididymal sperm maturation process is not well understood. Reference may be made to Hoskins D. D., Brandt H. and Acott T. S., *Fed Proc*, 37, 2534–2542, 1978; Majumder G. C., Dey C. S., Halder S. and Barua M., *Arch Androl*, 24, 287–303, 1990. Epididymal plasma (EP)/seminal plasma (SP) possess a factor that induces forward motility (FM) in vitro in the caput epididymal immature sperm derived from bull. Reference may be made to Acott, T. S., and Hoskins, D. D. *J Biol Chem*, 253, 6744–6750, 1978, Hoskins, D. D., Brandt, H. and Acott, T. S. *Fed. Proc.* 37, 2534–2542, 1978. In the case of hamster reference may be made to Cornwall, G. A., Smyth, T. S., Vindivich, D., Harter, C., Robinson, J. and Chang, T. S. K. *Biol Reprod* 35, 1065–1074, 1986. And in case of goat reference may be made to Jaiswal, B. S. and Majumder, G. C., *Int J Androl*, 19, 97–102, 1996. Hoskins and his associates (Acott, T. S. and Hoskins, D. D. *J Biol Chem*, 253, 6744–6750, 1978, Hoskins, D. D., Brandt, H. and Acott, T. S. *Fed. Proc.* 37, 2534–2542, 1978) have partially purified the active principle from bovine SP and EP and it has been designated as forward motility protein (FMP). FMP originates from epididymis, after its synthesis in epididymis the factor is secreted into epididymal plasma and subsequently it passes to seminal plasma (Brandt, H., Acott, T. S, Johnson, D. J. and Hoskins, D. D. *Biol. Reprod.* 19, 830–835, 1978). For the isolation of FMP, these investigators have used several fractionation techniques as elaborated below. The bovine SP was heated at 90° C. for 10 min. and then centrifuged at 1,78,000 xg for 60 min to remove the precipitated proteins. The resulting supernatant fluid was subjected to Sepharose 6B chromatography using a buffer containing 4M urea, 100 mM NaCl, 10 mM dithiothreitol and 100 mM Tris-HCl, pH 7.5. By these procedures FMP was purified to about 15-fold. Alternatively the factor was also partially purified further by concanavalin A-agarose affinity chromatography of the heat-treated SP. FMP binds to concanavalin A and was eluted with 0.25 M-α-methyl-D-mannoside. The isolated FMP contained several proteins as shown by sodium dodecyl sulphate (SDS)-gel electrophoresis and the extent of purity of FMP is not known. By using similar methods FMP was isolated from bovine EP although the degree of its purification is not known. FMP is a 37 KDa heat-stable glycoprotein that is believed to be essential for the initiation of sperm FM during the epididymal sperm maturation. FMP induces forward motility in vitro in the bovine immature/immotile caput-epididymal spermtozoa.

OBJECT OF THE INVENTION

The main object of the present invention is to provide a process for the isolation of a purified new epididymal forward motility protein (FMP) from goat, specifically derived from EP of goat epididymis. Another object is to provide a process for the isolation of a novel FMP (125 KDa) from goat EP which is strikingly different from bovine FMP, as mentioned above. By the process of the present invention for the first time we have achieved complete purification of FMP: the physiological sperm motility initiator/activator from EP. The isolated FMP obtained by the process of the present invention is homogeneous as evidenced by native polyacrylamide gel electrophoresis (PAGE), high performance liquid chromatography (HPLC) and iso-electricfocusing techniques, implicating thereby that the purity of FMP is nearly 100%. The FMP (125 KDa) obtained is different from the 37 KDa FMP partially purified from bovine SP by Acott T. S. and Hoskins D. D., *J Biol Chem*, 253, 6744–6750, 1978. FMP is highly immunogenic and its antibody strongly inhibits FM of mature sperm thereby implicating that FMP has the potential to serve as a contraceptive vaccine. As the protein obtained by the process of the present invention has high efficacy for stimulating motility of mature spermatozoa, FMP has potentially for rectifying some of the problems of human infertility due to low sperm motility. The goat epididymal FMP obtained by the process of the present invention has a strikingly different molecular mass as compared to the serum motility-promoting proteins of human (approx 200 KDa). Reference may be made to Pat. No. WO 9012032, Oct. 18, 1990, U.S. Pat. No. 5,304,464, Apr. 19, 1994; U.S. Pat. No. 5,453,354, Sep. 26, 1995. It is also different from that from buffalo serum (66 KDa) which has been described and claimed in our Patent Application No. 637/DEL/96 dated Mar. 27, 1996 that has the potentiality for the treatment of human infertility due to low order of sperm motility.

DETAILED DESCRIPTION OF THE INVENTION

The present invention provides a purified new epididymal forward motility protein and a process for the isolation of the said epididymal forward motility protein useful as a fertility promoter/blocker which comprises subjecting goat epididymal plasma to multiple fractionations till purification to obtain purified new epididymal forward motility protein.

In an embodiment of the present invention the fractionation may be effected using methods such as ammonium sulphate fractionation, cation-exchange chromatography using diethylaminoethyl (DEAE)-cellulose/Sephadex as the ion-exchange resin, anion-exchange chromatography using carboxymethyl (CM)-cellulose/Sephadex as the ion-exchange resin, concanavalin A-Sepharose 4B affinity chromatography, chromatofocusing using polybuffer exchanger termed as PBE-94 resin, adsorption chromatography using alumina gel or hydroxyapatite of BioRad and molecular sieving chromatography using Sephacryl/Sephadex as the insoluble matrix of high performance liquid chromatography. The process of this invention comprises of (a) purification and characterization of a novel FMP and (b) the methodologies for its purification from goat EP. Our invention reports for the first time the purification to apparent homogeneity of FMP from EP. The purity of the isolated FMP has firmly been established by using multiple modern analytical techniques such as PAGE, HPLC, isoelectricfocusing, etc. The molecular mass of native FMP as determined by Sephacryl S-200 gel filtration, HPLC and native PAGE is approx 125 KDa. It is a dimeric protein of about 70 and 54 KDa subunits. The factor has high protein specificity and affinity for inducing FM in the immature epididymal sperm in vitro. FMP at 30 µg/ml level showed maximal motility-promoting activity. FMP is also capable of enhancing FM of the goat mature cauda sperm. $Ca^{2+}$ and $Mg^{2+}$ stimulate FMP activity. Treatment of spermatozoa with FMP caused a significant increase of the intrasperm level of cyclic AMP thereby suggesting that FMP stimulates sperm motility by activating membrane-bound adenyl cyclase. It is an acidic protein with isoelectric point (PI) of about 4.75. It is stable to heat treatment at 100° C. for 3 min. It is a glycoprotein that binds with high affinity to concanavalin A (Con A). It contains mannose, galactose and N-acetyl glucosamine approximately in the ratios of 6:1:6. FMP markedly loses its activity when incubated with α-mannosidase, β-N-acetyl glucosaminidase and proteolytic enzymes indicating that both the sugar and protein parts are essential for its biological activity. Immunoflorescence studies show that FMP is localized on the outer surface of the sperm with special reference to the head region. FMP is strongly immunogenic. Antibody against it markedly inhibits FM of mature goat sperm as well as the FMP-induced motility initiation invitro in the immature sperm. Using enzyme-linked immunosorbent assay (ELISA) the distribution of FMP has been analysed in a variety of tissue and in some body fluids. The specific activity of FMP is highest in epididymal plasma. FMP or/and immunologically crossreactive protein(s) are present is significant level in bone marrow and blood serum. The other tissue tested have low/insignificant levels of FMP. The factor occurs in sperm plasma membrane and the membrane-bound FMP level increases markedly during the epididymal sperm maturation. The purified protein (FMP) from goat EP, is a physiological motility-activity protein. FMP is a novel motility-promoting protein whose characteristics are clearly different from those reported in the literature (Acott, T. S. and Hoskins, D. D. *J. Biol. Chem.*, 253, 6744–6750, 1978).

The process of the present invention essentially consists of the isolation of FMP from goat cauda epididymal plasma and purification of the said protein. Epididymal plasma was first fractionated with ammonium sulphate. The motility promoter was sedimented with 30–70% saturation of the salt. The salt fraction of FMP was then subjected to an anion-exchange, resin such as DEAE-cellusose/Sephadex using low ionic alkaline buffer (e.g. 10 mM potassium phosphate, pH 8.0). The factor binds to the resin and it can be eluted from the column at higher concentration of salt such as 100–200 mM potassium phosphate, pH 8.0. The FMP can also be purified by cation-exchange chromatography using CM-cellulose/Sephadex as the resin and low ionic acidic buffer (e.g. 10 mM Na-acetate buffer, pH 5.6) when the motility promoter (FMP) does not bind to the resin. The partially purified FMP as obtained after ion-exchange chromatography, was purified further by concanavalin. A affinity chromatography using con A-Sepharose 4B affinity matrix. FMP binds to the matrix and can be eluted from the column with 0.25–0.50 M α-methyl. D-manopyranoside. The motility promoter can be purified further by chromatofocusing utilizing PBE 94 resin (Pharmacia) and polybuffer 74 as eluting buffer. The motility promoter was then subjected to adsorption chromatography using an insoluble gel suspension (e.g. alumina gel or hydroxyapatite gel bead of BioRad). For the adsorption studies low ionic buffer (e.g. 10–20 mM potassium phosphate, pH 7–8 may be used. The factor binds to the gel and can be eluted with a relatively high concentration of salt (e.g. 500 mM potassium phosphate buffer, pH 7.0 to 8.0). The partially purified FMP as obtained after adsorption chromatography, was further purified by molecular sieving chromatrography using Sephacryl/Sephadex as the insoluble matrix or HPLC column using phosphate buffer of varying pH values (6.9 to 7.5) and varying ionic strengths (100–150 mM). A suitable combination of these procedures lead to approx 200 to 500 fold-purification of the motility promoter from the epididymal plasma with recovery of approx 10 to 20% of the total activity present in the epididymal plasma.

This invention is also relating to pharmaceutical preparations comprising a macromolecule of proteinaceous nature which is essentially pure, has a molecular weight of about 125 KDa and activates sperm motility together with any suitable excipient. Examples of suitable excipients are culture media or other salt solutions. The pharmaceutical preparations are prepared according to methods known per se. The pharmaceutical preparations according to invention have potentially for treatment of infertility.

The process of the present invention is further being illustrated below with examples which should not be construed to limit scope of the invention.

EXAMPLE 1

Goat cuada epididymides were collected from the local slaughter houses EP was prepared from the cauda-epididymides as described earlier (Roy N., Majumder G. C. and Chakraborty C. K. *Andrologia*, 17, 200–206, 1985). During the extraction of EP it gets diluted with a modified Ringer's solution (RPS medium: 119 mM NaCl, 5 mM KCl, 1.2 mM $MgSO_4$, 10 mM glucose, 16.3 mM potassium phosphate, pH 6.9, penicillin, 50 units/ml). The prepared EP contains 5 to 10 mg protein/ml. EP contains FMP that causes in vitro initiation of FM in the immature caput-epididymal sperm as reported earlier (Jaiswal B. S. and Majumder G. C. *Int. J. Androl.* 19, 97–102, 1996).

For the isolation of FMP, 250 ml of EP was used that contained 8.8 mg protein/ml and 100 units of FMP/ml, one unit of FMP being defined as the amount of the factor that induces FM in 10% of the sperm cells. EP was first subjected to ammonium sulphate fractionation by using 0–30% and 30–70% saturation of ammonium sulfate. In each step, the protein suspension was centrifuged for 15 min at 18000 g and the sedimented protein pellet was dissolved in 10 mM potassium phosphate, pH 8.0, while the supernates were subjected to further saturation by the addition of the solid ammonium sulfate. Approx 90% of the FMP activity was sedimented by 30–70% saturation of ammonium sulfate. The active fraction from $(NH4)_2SO_4$ fractionation was dialysed against 10 mM potassium phosphate buffer, pH8.0. The FMP obtained was then purified further by ion-exchange chromatography on a column (0.75×7.5 cm) of DEAE-cellulose previously equilibrated with 10 mM potassium phosphate buffer, pH 8.0. FMP binds to the resin and the major amount of FMP activity was eluted with a linear gradient of potassium phosphate buffer (165–185 mM), pH 8.0. The active FMP fractions were pooled and concentrated by Amicon ultrafiltration through PM-30 membrane. The FMP preparation was then dispersed in buffer-I (20 mM Tris-HCl,pH 7.2, 1.0 mM $CaCl_2$, 1.0 mM $MgCl_2$ and 1.0 mM $MnCl_2$) and then subjected to ConA-Sepharose affinity chromatography. The sample was applied to a ConA-Sepharose column (1×12 cm) previously equilibrated with buffer-I. FMP binds to the resin and it was eluted with 0.5 M α-methyl D-mannopyranoside.

FMP was further purified by chromatofocusing on PBE-94:a Pharmacia product. A column of (0.7×10 cm) of ion-exchange resin PBE-94, was equilibrated with 25 mM imidazole-HCl, pH 7.4 and FMP sample was applied to it. As the sample passed through, the column was washed with the equilibrating buffer. FMP was then eluted from the column with polybuffer 74-HCl, pH 4.0 (Pharmacia), the volume of each fraction being 1 ml. The active FMP fractions were pooled, concentrated by Amicon ultrafiltration using PM -30 membrane and finally dialysed against 10 mM potassium phosphate buffer, pH 7.5. The resulting FMP preparation was mixed with 10 ml of alumina gel (250 mg/ml, Sigma Chemical Co.) suspended in 10 mM potassium phosphate buffer, pH 7.5. The mixture was stirred for 1 hr at 4° C. The suspension was then centrifuged at 500 g for 10 min. The supernatant (unadsorbed fraction) was rejected and the bound FMP was eluted with 0.5M potassium phosphate, pH 7.5. The FMP preparation was concentrated by ultrafiltration through Amicon PM-30 membrane and dispersed in RPS medium, pH 6.9. FMP was then chromatographed on a Sephacryl S-200 gel filtration column (0.9×50 cm) equilibrated with RPS medium, pH 6.9. Elution was carried out with the equilibrating buffer, fractions (1 ml each) were collected in a LKB fraction collector and protein contents of the fractions were monitored by absorbence at 280 nm. The active fractions were pooled and concentrated by Amicon ultrafiltration using PM-30 membrane. All the purification steps were carried out at 0–4° C. By these procedures FMP was purified to approx 500-fold, the specific activity of the purified factor being about 5000 units/mg protein. The isolated FMP was approx 100% pure. The yield of pure FMP was approx 0.6 mg from 250 ml of EP preparation and the overall recovery of its activity was about 12%.

EXAMPLE 2

Goat cauda-epididymides were collected from the local slaughter houses. EP was then prepared from cauda epididymis as reported earlier (Roy, N., Majumder, G. C. and Chakrabory, C. K. *Andrologia,* 17, 200–206, 1985). During the extraction of EP, it gets diluted with the RPS medium, EP extract (500 ml: 9.6 mg protein/ml) was then subjected to ammonium sulphate fractionation by using 0–30% and 30–70% saturation of ammonium sulfate. In each step, the protein suspension was centrifuged for 15 min at 18000 g and the sedimented protein pellet was dissolved in 10 mM potassium phosphate. pH 8.0, while the supernates were subjected to further saturation by the addition of the solid ammonium sulfate. Approx 90% of the FMP activity was sedimented by 30–70% saturation of ammonium sulfate. The active ammonium sulfate fraction was dialysed against 10 mM sodium acetate buffer, pH 5.6 and then subjected to CM-cellulose chromatography. The resin was equilibrated with 10 mM Na-acetate buffer, pH 5.6. After passage of the sample, the column was washed with the equilibrating buffer. The column was then eluted successively with 50 ml each of 10 mM Na-acetate buffer, pH 5.6 containing 0.1M, 0.2M, 0.5M, and 1M NaCl. Major portion of FMP (approx 95%) did not bind to the resin. The unretained fraction of FMP was concentrated by Amicon ultrafiltration using PM-30 membrane and dialysed against buffer-I. The dialysed FMP fraction was then subjected to ConA-Sepharose affinity chromatography. FMP binds to the Con A affinity matrix. After proper washing of the column with buffer-I, FMP was eluted with 0.5M α-methyl-D-mannopyranoside. Active FMP fraction was then concentrated by Amicon ultrafiltration using PM-30 membrane and then dialysed against phosphate-buffered saline (PBS: 50 mM sodium phosphate containing 0.9% NaCl, pH 7.0). The dialysed FMP was then chromatographed on a Sephacryl S-200 gel filtration column (1×50 cm) previously equilibrated with PBS. 1 ml fractions were collected in a LKB fraction collector. Elution profile of FMP was monitored by absorbance at 280 nm. The active FMP fraction were pooled, concentrated by Amicon ultrafiltration using PM-30 membrane and dialysed against 10 mM potassium phosphate buffer, pH 8.0. The resulting FMP preparation was then applied to a hydroxyapatite column (1×5 cm). FMP adsorbed on hydroxyapatite gel, was eluted with 100 mM potassium phosphate buffer, pH 8.0 The active FMP fractions were pooled, concentrated by Amicon ultrafiltration and stored at −70° C. All the isolation steps were conducted at 0–4° C. The factor was purified to approx 400-fold with about 20% recovery. The isolated FMP was approx 90% pure. About 2.6 mg of the partially purified FMP was obtained from 500 ml of EP preparation (containing about 4.8 g protein).

The main advantages of the present invention are that it has developed a new product from epididymis that has potentiality for multiple uses:

1. Antibody of FMP strongly inhibits the sperm-forward motility which is essential for the fertility of the male gametes indicating that FMP antibody has potential to block male fertility. Thus FMP has potential to serve as a contraceptive vaccine.

2. One of the important reasons for human infertility is low sperm motility. As a promoter of sperm forward motility which is essential for sperm fertility, it has potentially for rectifying some of the problems of human infertility.

3. Any defect in motility of spermatozoa derived from the farm animals will also have an adverse affect on the breeding of these animals. It is well documented that animal products play an important role in the global economy. As a promoter of sperm forward motility, FMP thus have a tremendous applied potentiality for improving the breeding of farm animals thereby enhancing the production of a variety of animal products such as milk, meat, leather, wool, etc.

We claim:

1. A goat forward motility glycoprotein isolated and purified from goat epididymal plasma, having a molecular mass of about 125 Kda, and comprising mannose, galactose and N-acetyl glucosamine sugar residues.

2. The forward motility glycoprotein as claimed in claim 1, comprising two subunits of 70 and 54 KDa.

3. The forward motility glycoprotein as claimed in claim 1, having an isoelectric point of 4.75.

4. The forward motility glycoprotein as claimed in claim 1, which is activated by $Ca^{2+}$ and $Mg^{2+}$.

5. The forward motility glycoprotein of claim 1, which is active at 100° C. for 3 min.

6. The forward motility glycoprotein of claim 1 wherein the mannose, galactose, and N-acetyl glucosamine are in the ratio of about 6:1:6.

7. The forward motility protein as claimed in claim 1, which is optimally active at 30 µg/ml level for activating sperm forward motility.

8. The forward motility glycoprotein of claim 1 which is immunogenic.

* * * * *